United States Patent [19]

John et al.

[11] Patent Number: 5,424,465
[45] Date of Patent: Jun. 13, 1995

[54] PREPARATION OF 13-(Z)-RETINOIC ACID

[75] Inventors: Michael John, Ludwigshafen; Joachim Paust, Neuhofen, both of Germany

[73] Assignee: BASF Aktiengesellschaft, Ludwigshafen, Germany

[21] Appl. No.: 220,495

[22] Filed: Mar. 31, 1994

[30] Foreign Application Priority Data

Apr. 22, 1993 [DE] Germany .......................... 43 13 089.5

[51] Int. Cl.⁶ ............................................ C07C 51/353
[52] U.S. Cl. ................................... 554/125; 554/126; 204/157.67
[58] Field of Search ................ 554/125, 126; 585/371; 574/725; 204/157.67

[56] References Cited

U.S. PATENT DOCUMENTS 4,556,518 12/1985 Lucci .................................. 260/413

FOREIGN PATENT DOCUMENTS 1142657 9/1979 Canada .
111325 6/1984 European Pat. Off. .

OTHER PUBLICATIONS

Muccino et al., *J. Labelled Cmpd. Radiopharm.*, vol. 17, No. 3, 1980, pp. 463–469.
Garbers et al., *J. Chem. Soc.*, No. 16, 1968, pp. 1982–1983.
Carotenoids and Related Compounds . . . , J. Chem. Soc.(C), 1968, Pattenden et al.

Primary Examiner—José G. Dees
Assistant Examiner—Deborah D. Carr
Attorney, Agent, or Firm—Keil & Weinkauf

[57] ABSTRACT 13-(Z)-Retinoic acid is prepared by
 a) reacting 5-hydroxy-4-methyl-2(5H)-furanone with a [3-methyl-5-(2,6,6-trimethyl-1-cyclohexen-1-yl)-2,4-pentadienyl]triarylphosphonium salt and
 b) subsequently partially isomerizing the resulting mixture of 13-(Z)- and 11,13-di-(Z)-retinoic acid, where the reaction in step a) is carried out in the presence of lithium hydroxide as alkali metal hydroxide and in dimethylformamide as solvent at from +10° to −9° C. and/or the isomerization in step b) is carried out by irradiating the mixture of isomers obtained in a) in an organic solvent in the presence of a photosensitizer with light in the wavelength range from 200 to 600 nm.

6 Claims, No Drawings

PREPARATION OF 13-(Z)-RETINOIC ACID

BACKGROUND OF THE INVENTION

The present invention relates to the preparation of 13-(Z)-retinoic acid (I) by reacting 5-hydroxy-4-methyl-2(5H)-furanone (II; butenolide) with a [3-methyl-5-(2,6,6-trimethyl-1-cyclohexen-1-yl)-2,4-pentadienyl]-triarylphosphonium salt ($C_{15}$-triarylphosphonium salt) and subsequently partially isomerizing the resulting mixture of 13-(Z)- and 11,13-di-(Z)-retinoic acid (also called 13-cis- and 11,13-di-cis-retinoic acid or -vitamin A acid).

13-(Z)-Retinoic acid is a substance of pharmacological importance for the treatment of acne. Its synthesis is relatively difficult because of the formation of double-bond isomers.

Thus, for example, a synthesis described in J. Chem. Soc. (C) (1968) 1984–97 from butenolide II and a $C_{15}$-triarylphosphonium salt in diethyl ether results in a mixture of 13-(Z)- and 11,13-di-(Z)-retinoic acid in a yield of 66 to 75% of theory, where the content of the 13-(Z)-isomers is only about 36%. Selective isomerization of the 11-(Z) double bonds in the presence of a 13-(Z) double bond proves impossible.

Furthermore, EP-B1-0 111 325 discloses a process for preparing 13-(Z)-retinoic acid by coupling a $C_{15}$-triarylphosphonium salt to the butenolide II and subsequently isomerizing in the presence of transition metal catalysts. This process is intrinsically good but has the disadvantage that the Wittig reaction must be carried out at, preferably, from $-30°$ to $-45°$ C., which entails very high energy costs. In addition, an elaborate extraction procedure is necessary.

The subsequent selective isomerization of 11,13-di-(Z)-retinoic acid takes place in very good yields but the use of the isomerization catalysts described therein leads to contamination of the required product with traces of transition metals, which may lead to problems with the stability of the required product. Contamination of the required product with organic phosphorus from the addition of triphenylphosphine to decomplex the catalyst makes additional purification steps necessary. Furthermore, treatment of the required product with acetonitrile as solvent for the isomerization catalyst is not without problems.

SUMMARY OF THE INVENTION

It is an object of the present invention to improve the process for preparing 13-(Z)-retinoic acid by reacting a $C_{15}$-triarylphosphonium salt and butenolide II in the presence of an alkali metal hydroxide in an organic solvent and subsequently partially isomerizing in such a way that the Wittig reaction can be carried out at temperatures which are more advantageous in terms of energy and without the other prior art disadvantages with very good yields of pure 13-(Z)-retinoic acid.

We have found that this object is achieved by reacting a $C_{15}$-triarylphosphonium halide or hydrogen sulfate with butenolide II at from $+10°$ to $-9°$ C., which gives yields of up to 97.5% of theory when the reaction is carried out in dimethylformamide (DMF) as solvent and with lithium hydroxide as alkali metal hydroxide, and the butenolide is introduced into a mixture of the $C_{15}$-triarylphosphonium salt and LiOH in DMF.

This result was very surprising because the yields which can be obtained at these temperatures with other basic compounds such as potassium methylate, sodium carbonate, sodium hydroxide or potassium tert-butylate in other solvents used for this reaction, such as lower alcohols, heptane/water mixtures or DMF, were only about 21.3 to 44.5% of theory. For example, the yield of a mixture of retinoic acid isomers from a reaction in the presence of NaOH in DMF under conditions which were otherwise the same was only 35% of theory.

We have also found that the mixture of 13-(Z)- and 11,13-di-(Z)-retinoic acid obtained in the Wittig reaction described above can very advantageously be isomerized selectively to 13-(Z)-retinoic acid when the mixture of isomers is irradiated in an organic solvent, preferably in a lower alkanol, in the presence of a suitable photosensitizer with light in the wavelength range from about 200 to 600 nm.

The present invention therefore relates to a process for preparing 13-(Z)-retinoic acid of the formula I

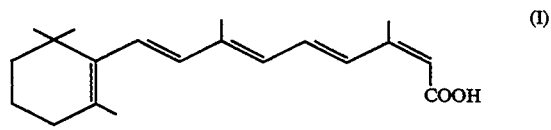

by a) reacting 5-hydroxy-4-methyl-2(5H)-furanone of the formula II

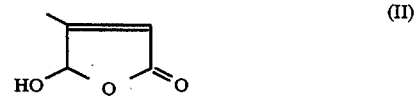

with a $C_{15}$-triarylphosphonium salt of the formula III

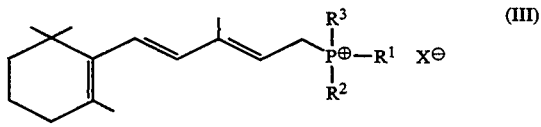

where $R^1$, $R^2$ and $R^3$ are each aryl, preferably phenyl, and $X^\ominus$ is halogen or $HSO_4^-$, in the presence of an alkali metal hydroxide in an organic solvent and b) subsequently partially isomerizing the resulting mixture of 13-(Z)- and 11,13-di-(Z)-retinoic acid, wherein the 5-hydroxy-4-methyl-2(5H)-furanone of the formula II is reacted in step a) with a mixture of the $C_{15}$-triarylphosphonium salt of the formula III and lithium hydroxide as alkali metal hydroxide in dimethylformamide as solvent at from $+10°$ to $-9°$ C., preferably $+5°$ to $-5°$ C., in particular $-2°$ to $+2°$ C.

The process according to the invention is particularly advantageous when a mixture of 13-(Z)- and 11,13-di-(Z)-retinoic acid is isomerized in step b) by irradiation in an organic solvent, preferably a $C_1$–$C_4$-alkanol, in particular in isopropanol, in the presence of a photosensitizer, preferably in the presence of erythrosin B, with light in the wavelength range from 200 to 600 nm.

The present invention therefore also relates to a process for preparing 13-(Z)-retinoic acid of the formula I

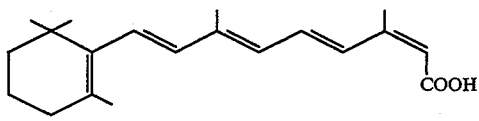

(I)

by
a) reacting 5-hydroxy-4-methyl-2(5H)-furanone of the formula II

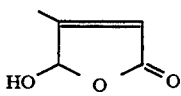

(II)

with a $C_{15}$-triarylphosphonium salt of the formula III

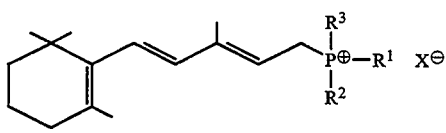

(III)

where $R^1$, $R^2$ and $R^3$ are each aryl, preferably phenyl, and $X^{\ominus}$ is halogen or $HSO_4^-$, in the presence of an alkali metal hydroxide in an organic solvent and b) subsequently partially isomerizing the resulting mixture of 13-(Z)- and 11,13-di-(Z)-retinoic acid, wherein the isomerization of the mixture of 13-(Z)- and 11,13-di-(Z)-retinoic acid in step b) is carried out by irradiating this mixture in an organic solvent, preferably a $C_1$-$C_4$-alkanol, in the presence of a photosensitizer, preferably in the presence of erythrosin B, with light in the wavelength range from 200 to 600 nm.

The 5-hydroxy-4-methyl-2(5H)-furanone used as starting compound is commercially available and can be prepared by acetal cleavage and intramolecular cyclization from β-formylcrotonic ester acetal.

The $C_{15}$-triarylphosphonium salts, in particular the $C_{15}$-triphenylphosphonium salts, of the formula III are readily available industrially since they are essential intermediates of one of the industrial vitamin A syntheses.

The Wittig reaction in stage a) is advantageously carried out by suspending the lithium hydroxide in dimethylformamide (DMF) and cooling the suspension to 0° C. To the cooled suspension are slowly added, firstly, a solution of the $C_{15}$-triarylphosphonium salt in DMF and then a solution of 5-hydroxy-3-methyl-2(5H)-furanone in DMF. The mixture is stirred at from +10° to −9° C., preferably +5° to −5° C. in particular +2° to −2° C., for 2-10, preferably 3-5, hours, and then ice-water is added. The water/DMF phase is then extracted, for example with hexane, and subsequently acidified and extracted with a hexane/ethyl acetate mixture. The organic phase is washed with water and the solvent is removed at about 40° C.

The amount of lithium hydroxide used in this case is from 2 to 6 mol, preferably 3 to 5 mol, per mol of $C_{15}$-triarylphosphonium salt.

The amount of DMF used is generally from 2 to 8 liters (l), preferably 3 to 6 l, based on 1 mol of $C_{15}$-triarylphosphonium salt.

The extractant advantageously used is hexane or a mixture of hexane and ethyl acetate. However, it is also possible to use all other organic solvents which are immiscible with water, such as ether, aliphatic hydrocarbons, halogenated and aromatic hydrocarbons, for the extraction of the mixture of retinoic acid isomers.

In this extraction, the DMF remains in the aqueous phase and keeps the triphenylphosphine oxide which is formed in the Wittig reaction in solution in the aqueous phase. This results in a further advantage compared with the process of EP 111 325, in which some of the triphenylphosphine oxide passes into the organic phase containing the required product and can be removed therefrom only at considerable expense.

The Wittig reaction described above results in a mixture of 13-(Z)- and 11,13-di-(Z)-retinoic acid in yields of from 95 to 98% of theory.

This mixture can be fractionated by conventional methods, for example by fractional crystallization, and the 11,13-di-(Z) isomer which is removed in this way can be converted into the 13-(Z) isomer. However, the resulting mixture of isomers is advantageously subjected directly to the isomerization.

Suitable solvents for the isomerization are those generally used for photoisomerization, such as aliphatic and cycloaliphatic hydrocarbons as well as halogenated aliphatic and aromatic hydrocarbons. $C_1$-$C_4$-Alkanols are particularly advantageous, especially isopropanol.

Suitable photosensitizers are readily available compounds which can be colored and/or fluorescent. Examples are 2,4,6-triphenylpyrylium perchlorate, 2,4,6-triphenylpyrylium picrate, 2,4,6-triphenylpyrylium chloroferrate, 2,4,6-tri(p-dimethylaminophenyl)-pyrylium perchlorate, 2,6-diphenyl-4-(p-dimethylaminophenyl)pyrylium chloride, perylene, quinizarin, β-quinophthalene, fluorescein, eosin, rose Bengal, erythrosin, euchrysin orange, rhodamine B and other rhodamines, diethylsafranin, astraphloxin, pseudoisocyanine and other cyanines, quinoline red or basacryl brilliant red, malachite green, methylene blue, crystal violet, 1,8-dihydroxy-4,5-diaminobromoanthraquinone, β-carotene, tetraphenylporphine and its metal complexes with Mg, Zn, Sn, Ni, Cu or Co, tetra(p-methoxyphenyl)porphine and its metal complexes, chlorophyll, hematoporphyrin and mixtures of two or more of the said sensitizers.

Erythrosin B is particularly advantageous.

Suitable sources of light in the wavelength range from 200 to 600 nm are Hg vapor lamps in various pressure ranges (high, medium and low pressure lamps).

The isomerization can be carried out at from −10° to 60° C., preferably from 0° to 30° C. Room temperature, ie. about 20° C., is particularly advantageous.

The isomerization generally takes from 10 to 60 minutes, preferably 15 to 35 minutes.

The 13-(Z)-retinoic acid obtained in this way crystallizes out of the isomerization solution and can be isolated therefrom in a purity which is at least 45% and is up to 99%. The remaining mother liquor can be returned to the isomerization apparatus.

EXAMPLE 1 a) 32.2 g of LiOH were suspended in 350 ml of dimethylformamide (DMF). The mixture was cooled to 0° C. and, over the course of 30 minutes (min) a solution of 143 g of 3-methyl-5-(2,6,6-trimethyl-1-cyclohexen-1-yl)-2,4-pentadienyl)triphenylphosphonium hydrogen sulfate in 333 g of DMF was added dropwise. Subsequently, over the course of 30 min, 52.3 g of 5-hydroxy-4-methyl-2(5H)-furanone (butenolide) in 263 g of DMF were added dropwise, and the mixture was stirred at 0° C. for 4 hours (h). Then 1050 ml of icewater were added. The water/DMF phase was extracted 3 times with 560 ml of n-hexane before it was adjusted to pH 3 with 42 ml of concentrated sulfuric acid. The mixture was then extracted twice with 800 ml of hexane/ethyl acetate (4:1). The organic phase was washed twice with 350 ml of water, and the solvent was completely removed at 40° C. under reduced pressure. The residue was dried at 75° C. under reduced pressure for 5 h and provided 76.7 g of retinoic acid in the form of a mixture of 13-(Z)- and 11,13-di-(Z)-retinoic acid. This corresponds to a yield of 97.5% of theory.

b) 62.5 g of the mixture of retinoic acid isomers obtained in a) were dissolved in 750 ml of isopropanol, and 1 ml of a 1% strength solution of erythrosin B in methanol was added. The resulting mixture was irradiated with UV light (wavelength 200 to 600 nm) in a circulating apparatus at room temperature (RT). The isomerization was complete after 30 min. The resulting crystals were filtered off and washed with 120 ml of cooled n-heptane. The required product was dried under a stream of nitrogen and was then 99% pure. The resulting mother liquor can be returned to the photoisomerization to form the required products. The yield of 13-(Z)-retinoic acid (crystalline) was 50% based on $C_{15}$-triphenylphosphonium salt.

EXAMPLE 2

57.3 g of a mixture of 13-(Z)- and 11,13-di-(Z)-retinoic acid prepared as in Example 1a were dissolved in 750 ml of methanol, and 1.2 ml of a 1% strength erythrosin B solution in methanol were added. The resulting reaction mixture was circulated in a photoreactor at RT while irradiating with light of a wavelength from 200 to 600 nm. The isomerization was complete after 30 min. The required 13-(Z)-retinoic acid crystallized out of the reaction solution and was filtered off. 27.5 g of crystalline required product, corresponding to a yield of 48%, were obtained.

EXAMPLE 3 (COMPARATIVE EXAMPLE)

20.4 g of 3-methyl-5-(2,6,6-trimethyl-1-cyclohexen-1-yl)-2,4-pentadienyl)triphenylphosphonium hydrogen sulfate were dissolved in 50 ml of DMF and, over the course of 30 min added dropwise to a suspension of 12.5 g of KOH in 50 ml of DMF at 0° C. Subsequently, at 0° C., 7.4 g of butenolide in 50 ml of DMF were added dropwise, and the mixture was then stirred at 0° C. for 30 min and subsequently 300 ml of water were added and the pH was adjusted to 2 by addition of concentrated sulfuric acid.

The mixture was then extracted as in Example 1 with a hexane/ethyl acetate mixture (4:1). 0.87 g of retinoic acid in the form of a mixture of 13-(Z)- and 11,13-di-(Z)-retinoic acid was obtained.

We claim:

1. A process for preparing 13-(Z)-retinoic acid of the formula

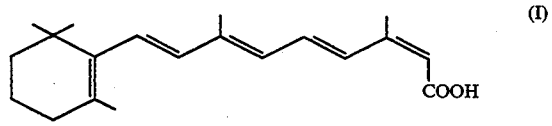

comprising the step of a) reacting 5-hydroxy-4-methyl-2(5H)-furanone of the formula II

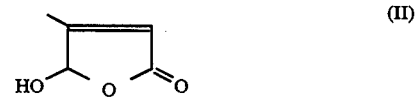

with a $C_{15}$-triarylphosphonium salt of the formula III

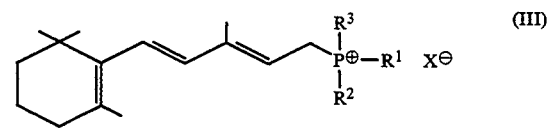

where $R^1$, $R^2$ and $R^3$ are each aryl and $X^\oplus$ is halogen or $HSO_4^-$, in the presence of lithium hydroxide in dimethylformamide at a temperature of from 10° to $-9°C$. until a mixture of 13-(Z)-retinoic acid and 11,13-di-(Z)-retinoic acid is formed, and then b) selectively isomerizing the 11,13-di-(Z)-retinoic acid in the mixture to 13-(Z)-retinoic acid.

2. A process for preparing 13-(Z)-retinoic acid as recited in claim 1, wherein the reaction of 5-hydroxy-4-methyl-2(5H)-furanone with $C_{15}$-triarylphosphonium salt is carried out at a temperature of from $+5°$ to $-5°$ C.

3. A process for preparing 13-(Z)-retinoic acid as recited in claim 1, wherein the $C_{15}$-triarylphosphonium salt is $C_{15}$-triphenylphosphoniumhydrogen sulfate.

4. A process for preparing 13-(Z)-retinoic acid as recited in claim 1, wherein the selective isomerization of 11,13-di-(Z)-retinoic acid is carried out by irradiating the mixture with light in the wavelength range from 200 to 600 nm in an organic solvent in the presence of a photosensitizer.

5. A process as recited in claim 4, wherein a $C_1$-$C_4$-alkanol is used as the organic solvent.

6. A process as recited in claim 4, wherein erythrosin B is used as the photosensitizer.

* * * * *